United States Patent
Van Os et al.

(10) Patent No.: US 10,300,297 B2
(45) Date of Patent: May 28, 2019

(54) LIGHT-EMITTING DEVICE AND PHOTO-THERAPY DEVICE COMPRISING A LIGHT-EMITTING DEVICE

(75) Inventors: Jacobos Petrus Johannes Van Os, Eindhoven (NL); Tim Dekker, Eindhoven (NL); Gerrit Oversluizen, Valkenswaard (NL); Paul Marcel Carl Lemmens, Veghel (NL); Frank Anton Van Abeelen, Eindhoven (NL); Wouter Hendrik Cornelis Spoorendonk, Enschede (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 917 days.

(21) Appl. No.: 14/123,826

(22) PCT Filed: Jun. 5, 2012

(86) PCT No.: PCT/IB2012/052822
§ 371 (c)(1),
(2), (4) Date: Dec. 4, 2013

(87) PCT Pub. No.: WO2012/172456
PCT Pub. Date: Dec. 20, 2012

(65) Prior Publication Data
US 2014/0094879 A1    Apr. 3, 2014

(30) Foreign Application Priority Data

Jun. 17, 2011 (EP) .................................... 11170450

(51) Int. Cl.
*A61N 5/06* (2006.01)
(52) U.S. Cl.
CPC ......... *A61N 5/0613* (2013.01); *A61N 5/0616* (2013.01); *A61N 2005/0629* (2013.01);
(Continued)

(58) Field of Classification Search
CPC .... A61N 5/0613; A61N 5/0616; A61N 5/062; A61N 2005/0626; A61N 2005/0629;
(Continued)

(56) References Cited

U.S. PATENT DOCUMENTS 5,616,140 A * 4/1997 Prescott ................... A61N 5/06
606/10
6,494,900 B1  12/2002 Salansky
(Continued)

FOREIGN PATENT DOCUMENTS

JP    2008539808 A    11/2007
JP    2009055969 A    3/2009
(Continued)

*Primary Examiner* — Ahmed M Farah (57) ABSTRACT

A light-emitting device (100) is disclosed. The light-emitting device (100) comprises a plurality of light-emitting elements (135) or light sources and a power module (120) adapted to selectively convey, supply or provide electrical power to the light-emitting elements (135). The power module (120) may be dimensioned such as to be able to power only a proper subset of the light-emitting elements (135) of the light-emitting device (100) at a given time, the subset having a maximum number of light-emitting elements (135) included therein with respect to the number of light-emitting elements (135) included in the all subsets of the light-emitting elements (135) of the light-emitting device (100). The plurality of sets of light-emitting elements (135) maybe arranged so as to emit light over a light emission area, and the plurality of sets of light-emitting elements (135) may be arranged relatively to each other such that different sets of light-emitting elements (135) emit light over different portions of the light emission area.

9 Claims, 8 Drawing Sheets

(52) U.S. Cl.
CPC ............... *A61N 2005/0645* (2013.01); *A61N 2005/0652* (2013.01)

(58) Field of Classification Search
CPC .... A61N 2005/0632; A61N 2005/0642; A61N 2005/0645; A61N 2005/0651; A61N 2005/0652
USPC ............... 607/88–92; 606/9–13; 128/898
See application file for complete search history.

(56) References Cited

U.S. PATENT DOCUMENTS

| | | | | |
|---|---|---|---|---|
| 6,602,275 | B1* | 8/2003 | Sullivan | A61N 5/0616 606/10 |
| 6,955,684 | B2* | 10/2005 | Savage, Jr. | A61N 5/0618 607/88 |
| 7,503,927 | B1* | 3/2009 | Vetanze | A61N 1/0408 607/115 |
| 2002/0188334 | A1 | 12/2002 | Carlgren | |
| 2003/0023283 | A1* | 1/2003 | McDaniel | A61K 8/02 607/88 |
| 2004/0044384 | A1* | 3/2004 | Leber | A61N 5/0619 607/88 |
| 2005/0187596 | A1 | 8/2005 | Fiset | |
| 2007/0129776 | A1 | 6/2007 | Robins | |
| 2007/0156208 | A1* | 7/2007 | Havell | A61N 5/0616 607/88 |
| 2010/0087898 | A1 | 4/2010 | Clement | |

FOREIGN PATENT DOCUMENTS

| | | |
|---|---|---|
| WO | 2007027962 A2 | 3/2007 |
| WO | 2007119084 A1 | 10/2007 |
| WO | 2008140855 A2 | 11/2008 |
| WO | 200959270 A1 | 5/2009 |

* cited by examiner

LIGHT-EMITTING DEVICE AND PHOTO-THERAPY DEVICE COMPRISING A LIGHT-EMITTING DEVICE

CROSS-REFERENCE TO PRIOR APPLICATIONS

This application is the U.S. National Phase application under 35 U.S.C. § 371 of International Application No. PCT/IB2012/052822, filed on Jun. 5, 2012, which claims the benefit of European Patent Application No. 11170450.8, filed on Jun. 17, 2011. These applications are hereby incorporated by reference herein.

FIELD OF THE INVENTION

The present invention generally relates to the field of lighting. Specifically, the present invention relates to light-emitting devices and photo-therapy devices comprising a light-emitting device.

BACKGROUND OF THE INVENTION

A photo-therapy device generally comprises a light-emitting device including e.g. one or more light-emitting diodes (LEDs) or a laser for causing a light induced effect e.g. on a skin area of a subject that is treated, by illuminating or irradiating the skin area with light emitted from the light-emitting device. Effectiveness of such treatment may at least partly depend on the amplitude of the light output or irradiance. For practical and functional reasons, it is often desired in photo-therapy devices to have a light-emitting device that emits light in a pulsed manner.

A light-emitting device of a photo-therapy device generally comprises a power supply and a current driver for driving the light source or light sources of the light-emitting device. Such a current driver may be relatively expensive, which adds to the manufacturing costs of the light-emitting device, and hence to the manufacturing costs of the photo-therapy device. It would be desirable to be able to reduce the manufacturing costs of such light-emitting devices.

WO2009/59270A1 discloses a light-emitting device for treating skin. The light-emitting device is composed of two units, one which contains a power module and one which produces light. One power unit can be used to power multiple light units. The device may be composed of multiple light units which can operate at the same time or independently.

For LED-based photo-therapy devices, about one third of the power dissipated in the LED or LEDs may be converted to light with the remainder of the power dissipated in the LED or LEDs being converted to heat. The fraction of power dissipated in a LED that is converted to light may depend on luminous efficacy of the LED, heat management in the photo-therapy device, etc. In particular for a portable photo-therapy device, the photo-therapy device may have a limited battery capacity, thereby limiting the available operating time of the photo-therapy device before its battery or batteries have to be recharged or replaced. Particularly for LED-based photo-therapy devices intended for application close to the skin of a subject, the heat generated by power dissipated in the LED or LEDs being converted to heat may conduct or transfer to the skin and may result in an excessive heat load on the skin, which may lead to overheating, e.g. the skin temperature at some position in the skin exceeding some threshold temperature value. The heat load is spread in the subject's body from the portion of the skin that is illuminated or irradiated by the photo-therapy device by means of blood flow in the body. A way of protecting the skin from overheating or eliminating or lessening the risk of the skin overheating as a result of operation of a LED-based photo-therapy device close to the skin is desired.

A photo-therapy device may generate a relatively high degree of illumination or irradiation, or "dose" of illumination or irradiation, which for example may be expressed in terms of irradiation energy per unit area of skin. There may be restrictions on the magnitude of the allowed daily dose of illumination. By operation of the photo-therapy device, the allowed daily dose may be reached in a relatively short treatment time. It would be desirable to be able to prolong the treatment time while at the same time following restrictions on the magnitude of the allowed daily dose of illumination.

SUMMARY OF THE INVENTION

In view of the above discussion, a concern of the present invention is to provide a light-emitting device for which manufacturing costs are reduced.

Another concern of the present invention is to provide a light-emitting device suitable for photo-therapy or cosmetic applications that may prolong the treatment time while at the same time following the restrictions on the magnitude of an allowed daily dose of illumination.

Another concern of the present invention is to provide a light-emitting device suitable for photo-therapy or cosmetic applications that may prolong the treatment time while not requiring an increase in power available for operation of the light-emitting device, e.g. by means of an increase in battery capacity.

In the context of the present application, by "treatment time" it is meant a time period in which treatment by means of illumination of e.g. skin of a subject by means of the light-emitting device may take place so as to not exceed the magnitude of an allowed daily dose of illumination.

Another concern of the present invention is to provide a light-emitting device suitable for photo-therapy or cosmetic applications that may alleviate or eliminate the risk of the treated skin being overheated as a result of the treatment.

To address these concerns and other concerns, light-emitting devices in accordance with the independent claims are provided. Preferred embodiments are defined by the dependent claims.

According to a first aspect of the present invention, there is provided a light-emitting device comprising a light-emitting module and a power module.

The light-emitting module comprises a plurality of sets of light-emitting elements.

The power module is adapted to selectively convey, i.e. supply or provide, electrical power to the plurality of sets, or to at least some of the plurality of sets, during respective non-overlapping time intervals for powering the respective sets.

The power module is configured such that it has an upper capacity limit with respect to electrical power that can be conveyed to each of the plurality of sets. The upper capacity limit of the power module corresponds to electrical power requirement of a set of the plurality of sets having a maximum number of light-emitting elements included therein with respect to the number of light-emitting elements included in the respective sets.

A gist of the present invention is to provide a light-emitting device which comprises a plurality of light-emitting elements or light sources and a power module adapted to selectively convey, supply or provide electrical power to the light-emitting elements, which power module is dimensioned such as to be able to power only a proper subset of the light-emitting elements of the light-emitting device at a given time. For example where the light-emitting elements comprise light-emitting diodes (LEDs) or the like, the power module may comprise a current driver, which can be used to regulate the current through the LEDs regardless of power supply variations, which e.g. may entail variations in output voltage of the power supply or changes in forward voltage drops between LEDs. In such a light-emitting device a maximum current requirement or current capacity requirement of the power module may be reduced compared to a light-emitting device that is able to power or drive each of the light-emitting elements simultaneously. The cost of the current driver typically increases with the maximum current that it is required to be able to handle. Hence, by limiting the maximum current requirement or current capacity requirement of the power module in this way, the cost of electronics required for manufacturing the light-emitting device may be reduced. Hence, by a light-emitting device according to the present invention manufacturing costs may be reduced.

In the context of the present application, by a proper subset of a set it is meant a set that is a subset of the set but not equal to it.

In many cases, both for practical and functional reasons, it is desired to have a light-emitting device that emits light in a pulsed manner, i.e. the light output from the light-emitting device is temporally and/or spatially distributed.

By means of the power module being adapted to selectively convey, supply or provide electrical power to the plurality of sets, or to at least some of the plurality of sets, during respective non-overlapping time intervals in order to power the respective sets, light output from the light-emitting device may be temporally distributed. This is further described in the following.

Optionally, light output from the light-emitting device may be spatially distributed. This is further described in the following.

Principles of the present invention are further described in the following. As indicated above, the power module may for example comprise an electrical current driver adapted to selectively convey electrical current to the plurality of sets during respective non-overlapping time intervals. The electrical current driver may be configured such that it has an upper capacity limit of electrical current that can be conveyed to the plurality of sets. In other words, the power module and/or the electrical current driver may be dimensioned so as to have the capacity to power only the largest set of the plurality of sets, or one of the largest sets of the plurality of sets, at a given moment.

In the context of the present application, by powering a set of the plurality of sets it is meant that each of the light-emitting elements included in the set being powered is powered, i.e. that a sufficient amount of current or power is supplied to the respective set so as to achieve that all of the light-emitting elements included in the set are powered and hence emitting light. In other words, by power requirement of a set of the plurality of sets of light-emitting elements it may mean the power that is required for achieving that all of the light-emitting elements in the set are operating, i.e. emitting light, simultaneously.

The power module and/or the electrical current driver in a light-emitting device according to the present invention may in general be less expensive compared to a power module and/or electrical current driver dimensioned so as to have the capacity to power all of the light-emitting elements simultaneously, since the power module and/or electrical current driver in the latter case would be required to be able to accommodate or handle larger currents compared to the power module and/or electrical current driver of a light-emitting device according to the present invention.

For conveying power to the respective sets of the plurality of sets, the light-emitting device and/or the power module may comprise a current and/or power multiplexer adapted to selectively channel or convey electrical current and/or power to the momentarily selected set of the plurality of sets.

The power module may be configured to generate power, e.g. by means of a battery.

A plurality of sets of light-emitting elements may according to one example comprise at least two sets of light-emitting elements.

A set of light-emitting elements may include a single light-emitting element only. In general, each set of light-emitting elements may include a plurality of light-emitting elements.

The upper capacity limit of the power module may be such so as to additionally accommodate for possible losses, e.g. resistive losses, during conveyance of the electrical power from the power module to the respective set of the plurality of sets. Such losses may for example occur in the electrical transmission path from the power module to the plurality of sets. The electrical transmission path may for example comprise electrical conductors connecting the power module with the plurality of sets.

The plurality of sets of light-emitting elements may be arranged so as to emit light over a light emission area.

The plurality of sets of light-emitting elements may be arranged relatively to each other such that different sets of light-emitting elements emit light over different portions of the light emission area.

Another gist of the present invention is that, in addition to the power module being dimensioned so as to be able to power only a proper subset of the light-emitting elements of the light-emitting device at a given time, the sets of light-emitting elements may be arranged relatively to each other such that different sets of light-emitting elements may emit light over different portions of a light emission area. This arrangement of the plurality of sets of light-emitting elements relatively to each other is described further in the following with respect to a second aspect of the present invention and embodiments thereof. In other words, the plurality of sets of light-emitting elements may be arranged such that the respective different portions of the light emission area are capable of being irradiated by respective light emission one at a time in a succession, possibly with a pause between successive light emission periods, i.e. such that there are periods when none of the plurality of sets of light-emitting elements are emitting light. Hence, there may be a temporal distance between conveyances of power to subsequently powered sets of the plurality of sets of light-emitting elements.

The light-emitting module may be arranged such that the plurality of sets of light-emitting elements are arranged in the light-emitting device relative to each other such that they are spatially separated relative to each other. Such a configuration may enable spatially distributing light output from the light-emitting device.

The light-emitting device may comprise a control module adapted to control operation of the light-emitting module and/or the power module.

The control module may be adapted to cause the power module to convey power consecutively, or sequentially, to the plurality of sets.

The control module may be adapted to cause the power module to convey power to the plurality of sets during respective non-overlapping time intervals such that there is a temporal distance, e.g. a time gap or delay, between conveyances of power to subsequently powered sets of the plurality of sets.

Hence, subsequently powered sets may be powered one after the other, with or without time gap or delay between powering of a first set and powering of a second set.

The control module may be adapted to convey power to the plurality of sets in such an order so as to maximize spatial separation between a first set of light-emitting elements being powered during a first time interval and a second set of light-emitting elements being powered during a second time interval, where the second time interval is subsequent or successive to the first time interval.

Specifically, the control module may be adapted to convey power to the plurality of sets in such an order so as to maximize average spatial separation between subsequently powered sets of the plurality of sets on basis of the arrangement of the plurality of sets relative to each other in the light-emitting device.

The power module may be adapted to continuously convey additional electrical power to the plurality of sets.

That is, in addition some power may be continuously conveyed to the plurality of sets.

Hence, in addition to the power module selectively conveying electrical power to the plurality of sets, or to at least some of the plurality of sets, during respective non-overlapping time intervals for powering the respective sets, the power module may further continuously convey additional electrical power to the plurality of sets.

For example, a fraction of the total power conveyed to a particular set of the plurality of sets during a respective time interval may be power that is conveyed to the particular set during the respective time interval only. The remaining fraction, e.g. a few percent, e.g. 5%, of the total power conveyed to the particular set during the respective time interval may be power that is conveyed continuously to the particular set.

According to a second aspect of the present invention, there is provided a light-emitting device comprising a light-emitting module and a power module. The light-emitting module comprises a plurality of sets of light-emitting elements. The power module is adapted to selectively convey, i.e. supply or provide, electrical power to the plurality of sets, or to at least some of the plurality of sets, during respective non-overlapping time intervals for powering the respective sets. The plurality of sets of light-emitting elements are arranged so as to emit light over a light emission area. The plurality of sets of light-emitting elements are arranged relatively to each other such that different sets of light-emitting elements emit light over different portions of the light emission area, or via different portions of the light emission area.

Yet another gist of the present invention is to provide sets of light-emitting elements that are arranged relatively to each other such that different sets of light-emitting elements may emit light over different portions of a light emission area, and a power module adapted to selectively convey, supply or provide electrical power to the light-emitting elements. In other words, the plurality of sets of light-emitting elements are arranged such that the different portions of the light emission area are capable of emitting light one at a time in a succession, possibly with a pause between successive light emission periods, i.e. such that there are periods when none of the plurality of sets of light-emitting elements are emitting light. Hence, there may be a temporal distance between conveyances of power to subsequently powered sets of the plurality of sets of light-emitting elements.

In other words, there is provided a light-emitting device comprising a plurality of sets of light-emitting elements, each of which sets is configured to emit light via different portions of a light emission area of the light-emitting device, e.g. so as to be capable of illuminating different portions of skin of a subject, and each of which sets can be individually and selectively switched on and off, or activated and deactivated. The plurality of sets of light-emitting elements may be sequentially operated, e.g. by means of a control unit or controller that may be included in the light-emitting device, one set of light-emitting elements at the time, possibly with an "off period", idle period or non-illumination period between two successive "on periods". Hence, a light-emission area selective and/or sequential operation of the plurality of sets of light-emitting elements of the light-emitting device may be achieved.

In the context of utilizing the light-emitting device according to the present invention in photo-therapeutic or cosmetic applications, while a portion of the skin being treated is being energized or illuminated, thermal relaxation of the rest of the skin being treated may take place. The "on periods" may be characterized by energizing or illuminating skin of a subject at a relatively high or maximum allowed illumination power. The duration of the "on periods" may be determined by or be based on a maximum allowable skin temperature. An effect of the "on periods" may be to stimulate a biochemical and/or blood perfusion effect in the skin of the subject, or in alternative additionally stimulating blood circulation in the subject. One or both of these effects may spatially extend to portions of the skin other than the portion or portions of the skin that are directly illuminated by the light-emitting device and/or be maintained during a time period after illumination of the portion or portions of the skin by means of the light-emitting device has been stopped. This is due to thermal relaxation of the body of a human subject. It may take time for the human body to spread the heat caused by the light-emitting device emitting light on the skin portion or portions, and hence to lower the skin temperature to a normal, nominal or baseline skin temperature after the illumination of the portion or portions of the skin by means of the light-emitting device has been stopped. During such a thermal relaxation time period, vasodilation, i.e. widening of blood vessels resulting from relaxation of smooth muscle cells within the vessel walls, may still be at an elevated level, i.e. exceeding a normal, nominal or baseline level.

The duration of at least one of the time intervals may be selected based on an estimation of heat generating capacity of the light-emitting device in a skin portion of a subject as a function of time caused by the light-emitting device emitting light on the skin portion and a maximum allowable temperature in the skin of the subject.

In the context of utilizing the light-emitting device according to the present invention in photo-therapeutic or cosmetic applications, the "off periods" may be characterized by thermal relaxation of the skin of a subject when there is no illumination of the portion or portions of the skin by means of the light-emitting device, however possibly with some heat generated in the skin of the subject by means of radiative heat transfer between a part or portion of the light-emitting device and the skin of the subject. The duration of the "off periods" may be determined by or be based on a maximum allowable or desirable decline during the "off periods" in the biochemical and/or blood perfusion effect in the skin of the subject that has been induced during the "on periods". For example, the duration of the "off periods" may be determined by or be based on a blood circulation value not falling below a predefined value, e.g. about two times a nominal or baseline blood circulation value, of blood circulation in the subject.

Thus, operation of the power module may be controlled, e.g. by means of a control module, so as to cause the power module to convey power to the plurality of sets during respective non-overlapping time intervals such that there is an idle time period, or "off" period, having a selected duration, between conveyances of power to subsequently powered sets of the plurality of sets.

The durations of idle time periods between conveyances of power to different subsequently powered sets of the plurality of sets may be the same or different.

The durations of idle time periods between conveyances of power to different subsequently powered sets of the plurality of sets may be individually selected with respect to different subsequently powered sets of the plurality of sets.

The duration of the idle time period may be selected based on at least one of: an estimation of the heat transporting capacity of the blood flow in the skin of a subject, measurement of temperature in the skin of the subject, and a measurement of skin blood perfusion in the subject.

By the plurality of sets of light-emitting elements of the light-emitting device, where each of which sets is configured to emit light via different portions of a light emission area of the light-emitting device, e.g. so as to be capable of illuminating different portions of skin of a subject, and each of which sets can be individually and selectively switched on and off, or activated and deactivated, the overall treatment time may be increased compared to if all light-emitting elements in the light-emitting device for photo-therapy were to be activated simultaneously during a time period. This is due to the fact that the entire skin portion to be treated is not treated at the same time but for example sequentially, and possibly with pauses between the light emission periods, so that locally on the skin portion to be treated the build-up of the allowed daily dose of illumination becomes slower compared to if all light-emitting elements in the light-emitting device for photo-therapy were to be activated simultaneously during a time period. The increase in treatment time may be achieved while an increase in power available for operation of the light-emitting device, e.g. by means of an increase in battery capacity, may not be required. Since only one set of the plurality of sets of light-emitting devices is powered at a time, or in other words since only the light-emitting elements of one set at a time emit light, the risk that the skin portion being treated becomes overheated as a result of the treatment may be alleviated or eliminated. The heat load is spread in the subject's body by means of blood flow in the body from the skin portion being treated. With only a portion of the skin portion being treated being illuminated at a time, the heat load may be spread more quickly by means of the blood flow compared to a situation wherein the entire skin portion being treated would be illuminated. In turn, the increase in skin temperature may be less compared to a situation wherein the entire skin portion being treated would be illuminated.

Operation of the power module may be controlled, e.g. by means of a control module, so as to cause the power module to convey power to the plurality of sets during respective non-overlapping time intervals until power has been conveyed to each set of the plurality of sets at least once.

Operation of the power module may be controlled, e.g. by means of the control module, so as to cause the power module to convey power to the plurality of sets such that there is a spatial separation between subsequently powered sets of the plurality of sets, on basis of the arrangement of the plurality of sets relatively to each other in the light-emitting device.

According to an embodiment of the second aspect of the present invention, the power module may be adapted to convey electrical power simultaneously to at least some of the plurality of sets during an initial illumination time period for powering the at least some of the plurality of sets prior to selectively conveying electrical power to the plurality of sets during respective non-overlapping time intervals for powering the respective sets. In other words, prior to the sequence of individually and selectively powering the plurality of sets, some or all of the sets may be powered simultaneously. In the context of utilizing the light-emitting device according to the present invention in photo-therapeutic or cosmetic applications, such a configuration may facilitate increasing vasodilation in a subject illuminated by the light-emitting device to an elevated level, exceeding a normal, nominal or baseline vasodilation level, or maintaining an elevated vasodilation level, prior to the light-emission area selective and/or sequential operation of the plurality of sets of light-emitting elements of the light-emitting device has begun.

The plurality of sets of light-emitting elements may for example be arranged so as to form columns and/or rows of light-emitting elements, e.g. such that each column or row corresponds to a set of the plurality of sets. The columns or rows may be arranged adjacent to each other so as to form the light emission area. However, the columns or rows may be spaced with respect to each other, i.e. there may be some space between neighboring columns or rows.

However, the arrangement of the plurality of sets is not limited to rows or columns of light-emitting elements. The plurality of sets of light-emitting elements may for example be arranged relatively to each other such that each of the portions of the light emission area comprises subportions that are spatially separated with respect to each other. For example, particularly in a case where the light-emitting elements are arranged so as to form an array or pattern when viewed from a certain direction, each set of the plurality of sets may be constituted by respective non-coinciding "dot patterns", where, for each "dot pattern", each "dot" is constituted by one or a few light-emitting elements. Such a configuration of the sets of light-emitting elements is described further in the following with reference to attached drawings.

The plurality of sets of light-emitting elements may be arranged such that the light-emitting device is adapted to generate heat in a portion of the skin of a subject caused by the light-emitting device emitting light over the light emission area onto the skin portion.

The light-emitting elements of each set of the plurality of sets of light-emitting elements may be arranged so as to extend along a direction perpendicular to a main blood flow direction in the portion of the subject when the light-emitting device is applied onto the skin. Such a configuration may, when properly temporally and/or spatially operated, increase heat spreading in the skin by means of blood flow and/or allow for an increased degree of light treatment.

The plurality of sets of light-emitting elements may be arranged relatively to each other such that each of the portions of the light emission area constitutes a fraction of the total light emission area that is less than or equal to about 25% of the total light emission area, preferably such that each of the portions of the light emission area constitutes a fraction of the total light emission area that is between about 5% and 20% of the total light emission area.

According to a third aspect of the present invention, there is provided a light-emitting device comprising a light-emitting module and a power module. The light-emitting module comprises a plurality of sets of light-emitting elements. The power module is adapted to selectively convey, i.e. supply or provide, electrical power to the plurality of sets, or to at least some of the plurality of sets, during respective non-overlapping time intervals for powering the respective sets. The power module is configured such that it has an upper capacity limit with respect to electrical power that can be conveyed to each of the plurality of sets. The upper capacity limit of the power module corresponds to an electrical power requirement of a set of the plurality of sets having a maximum number of light-emitting elements included therein with respect to the number of light-emitting elements included in the respective sets. The plurality of sets of light-emitting elements are arranged so as to emit light over a light emission area, and the plurality of sets of light-emitting elements are arranged relatively to each other such that different sets of light-emitting elements emit light over different portions of the light emission area.

Hence, according to the third aspect of the present invention, a light-emitting device configured in accordance with both the first and second aspects of the present invention or embodiments thereof as described in the foregoing is provided.

The light-emitting elements may for example comprise LEDs. Other types of light-emitting elements are also possible, for example light-emitting elements that readily can be used for providing pulsed light emission from the light-emitting device.

A light-emitting device according to the present invention may for example be utilized in photo-therapeutic or cosmetic applications.

To this end, according to a fourth aspect of the present invention, there is provided a photo-therapy or cosmetic device including a light-emitting device according to the present invention.

In the context of the present invention, by photo-therapy, or light therapy or heliotherapy, it is meant a procedure comprising exposing a subject to light, possibly having specific wavelengths, by means of light sources such as lasers, light-emitting diodes, fluorescent lamps, dichroic lamps, etc. This list is not exhaustive. The subject is typically exposed to light that may be directed to specific locations on the subject's body and/or for a duration defined by a predefined period of time. Photo-therapy is commonly used for treating skin disorders such as psoriasis, sleep disorders such as a circadian rhythm disorder, and pain management, although other applications are known as well. This list is not exhaustive.

It has been found that an improved treatment effectiveness in photo-therapeutic application may be attained by using pulsed light emission. Operation of a light-emitting device in pulsed manner may entail a reduced power requirement of the light-emitting device compared to using non-pulsed light emission. Using pulsed light emission in photo-therapeutic applications, the overheating of the skin being treated may be mitigated or even avoided. Possibly, pulsed light emission may have a positive effect on photobiology efficiency.

The light-emitting device may be adapted to emit light onto a skin portion of a subject, and the photo-therapy device may be arranged so as to be releasably connectable to the skin portion. For example, the photo-therapy device may comprise straps or the like for allowing the photo-therapy device or the light-emitting device to be releasably arranged onto a subject so as to be able to emit light onto a selected skin portion of the subject, e.g. a portion of the skin of an arm or leg of the subject. The photo-therapy device may for example be wearable on a selected skin portion of the subject similarly to how a wristwatch is worn on the wrist. According to another example, the photo-therapy device may be included in or be constituted by a pain relief patch or the like.

Further objects and advantages of the present invention are described in the following by means of exemplifying embodiments.

It is noted that the present invention relates to all possible combinations of features recited in the claims. Further features of, and advantages with, the present invention will become apparent when studying the appended claims and the following description. Those skilled in the art realize that different features of the present invention can be combined to create embodiments other than those described in the following.

BRIEF DESCRIPTION OF THE DRAWINGS

Exemplifying embodiments of the invention will be described below with reference to the accompanying drawings, in which.

In the accompanying drawings, the same reference numerals denote the same or similar elements throughout the views.

DETAILED DESCRIPTION

The present invention will now be described more fully hereinafter with reference to the accompanying drawings, in which exemplifying embodiments of the present invention are shown. The present invention may, however, be embodied in many different forms and should not be construed as limited to the embodiments set forth herein; rather, these embodiments are provided by way of example so that this disclosure will convey the scope of the invention to those skilled in the art. Furthermore, like numbers refer to like or similar elements or components throughout.

Figure 1:
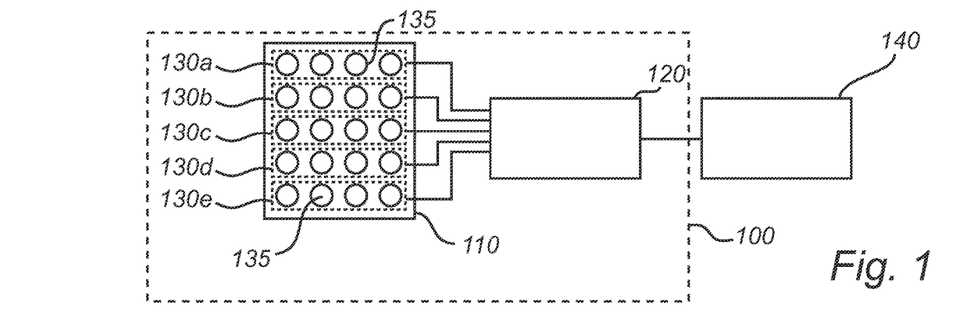
FIG. 1 is a schematic block diagram of a light-emitting device according to an exemplifying embodiment of the present invention.

Referring now to FIG. 1, there is shown a schematic block diagram of a light-emitting device 100 according to an exemplifying embodiment of the present invention.

The light-emitting device 100 comprises a light-emitting module 110 and a power module 120.

The light-emitting module 110 comprises a plurality of sets 130a-130e of light-emitting elements 135, indicated by circles in FIG. 1. Only a few of the light-emitting elements 135 shown in FIG. 1 are indicated by reference numerals. A light-emitting element 135 may for example comprise a light-emitting diode (LED).

Five sets 130a-130e of light-emitting elements 135 are shown in FIG. 1, where each set 130a-130e comprises four light-emitting elements 135. However, it is to be understood that the number of sets included in the light-emitting module 110 and the number of light-emitting elements 135 included in each set 130a-130e, respectively, in principle can be any positive integer, such as two, three, four, six, eight, ten, fifteen, twenty, thirty or fifty or larger.

The power module 120 is adapted to selectively convey, i.e. supply or provide, electrical power to the plurality of sets 130a-130e during respective non-overlapping time intervals for powering the respective sets 130a-130e.

According to the depicted embodiment, electrical power is generated by a power supply unit 140 connectable to the light-emitting device 100 via the power module 120. The power supply unit 140 may be adapted to supply direct current (DC) and/or alternate current (AC). The power module 120 may be configured depending on type(s) of current generated by the power supply unit 140, in order to be able to selectively convey DC and/or AC power to the plurality of sets 130a-130e depending on a possible requirement of the respective light-emitting elements 135.

The power module 120 is configured such that it has an upper capacity limit with respect to electrical power that can be conveyed to each of the plurality of sets 130a-130e. The upper capacity limit of the power module 120 corresponds to electrical power requirement of a set 130a-130e of the plurality of sets 130a-130e having a maximum number of light-emitting elements 135 included therein with respect to the number of light-emitting elements 135 included in the respective sets 130a-130e.

As mentioned above the light-emitting elements may comprise LEDs. LEDs may require current limiting when driven from a voltage source. In many applications it is desirable to drive LEDs with a constant-current driver. Such a current driver can be used to regulate the current through the individual LEDs regardless of power supply variations, which e.g. may entail variations in output voltage of the power supply or changes in forward voltage drops between LEDs.

To this end, the power module 120 may comprise an electrical current driver 120 adapted to selectively convey electrical current to the plurality of sets 130a-130e during respective non-overlapping time intervals. The electrical current driver 120 may be configured such that it has an upper capacity limit of electrical current that can be conveyed to the plurality of sets 130a-130e corresponding to electrical current requirement of a set of the plurality of sets having a maximum number of light-emitting elements included therein with respect to the number of light-emitting elements included in the respective sets.

The power module 120 may include its own power supply and hence a separate power supply unit 140 to which the power module 120 is connectable as shown in FIG. 1 may not be required.

The power supply 140 may comprise an internal power source, e.g. a battery (not shown in FIG. 1), or be electrically coupled to an external power source, e.g. a power grid (not shown in FIG. 1).

Optionally, the plurality of sets 130a-130e of light-emitting elements 135 may be arranged so as to emit light over a light emission area (not shown in FIG. 1). The plurality of sets 130a-130e of light-emitting elements 135 may be arranged relatively to each other such that different sets 130a-130e of light-emitting elements 135 emit light over different portions of the light emission area.

Figure 2:
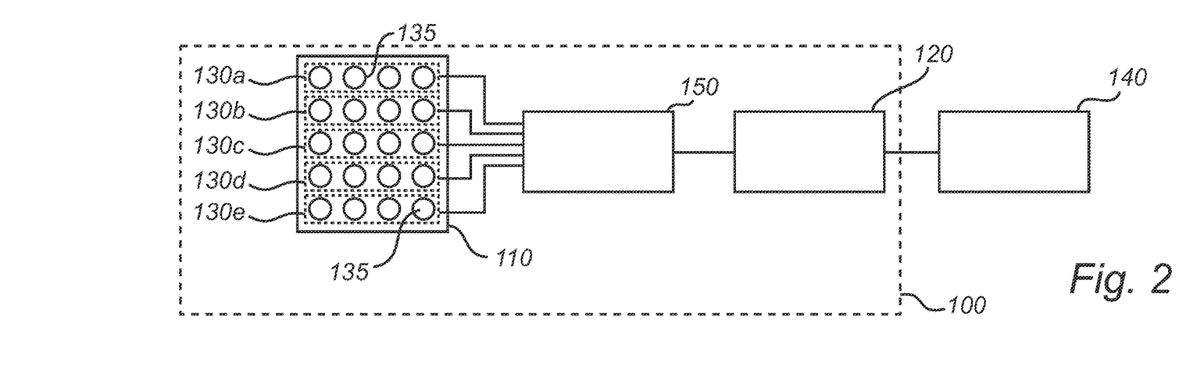
FIG. 2 is a schematic block diagram of a light-emitting device according to another exemplifying embodiment of the present invention.

Referring now to FIG. 2, there is shown a schematic block diagram of a light-emitting device 100 according to another exemplifying embodiment of the present invention.

Components indicated in FIG. 2 having corresponding reference numerals to components indicated in FIG. 1 are similar to or the same as the respective components described with reference to FIG. 1, and the functions thereof are similar to or the same as the functions of the respective components described with reference to FIG. 1.

For facilitating effectuating conveyance or supply of power to the respective sets 130a-130e of the plurality of sets 130a-130e, the light-emitting device 100 comprises a current and/or power multiplexer 150.

The current and/or power multiplexer 150 is adapted to selectively channel or convey electrical current and/or power to the at least momentarily selected set 130a-130e of the plurality of sets 130a-130e, i.e. the set 130a-130e that is to be at least momentarily powered.

Principles of selection of the set that is to be momentarily powered are described in the following with reference to FIG. 3.

Figure 3:
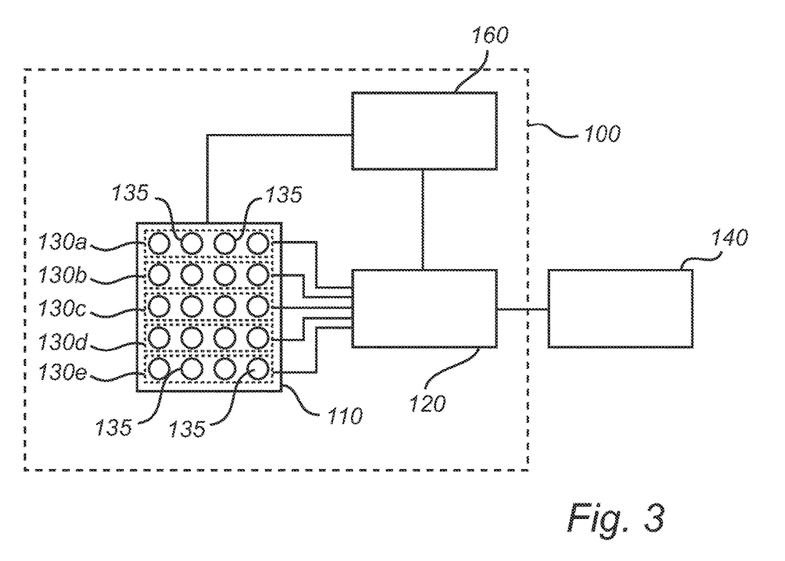
FIG. 3 is a schematic block diagram of a light-emitting device according to another exemplifying embodiment of the present invention.

FIG. 3 is a schematic block diagram of a light-emitting device 100 according to another exemplifying embodiment of the present invention.

Components indicated in FIG. 3 having corresponding reference numerals to components indicated in FIG. 1 are similar to or the same as the respective components described with reference to FIG. 1, and the functions thereof are similar to or the same as the functions of the respective components described with reference to FIG. 1.

The light-emitting device 100 comprises a control module 160. The control module 160 is adapted to control operation of the power module 120 and, optionally, the light-emitting module 110. The control module 160 can control operation of the light-emitting module 110 and the power module 120 independently of each other.

With regards to operation of the power module 120, the control module 160 can be adapted to cause the power module 120 to convey power consecutively, or sequentially, to the plurality of sets 130a-130e.

The control module 160 can be adapted to cause the power module 120 to convey power to the plurality of sets 130a-120e during respective non-overlapping time intervals in such a way that there is a temporal distance, e.g. a time gap or delay, between conveyances of power to subsequently powered sets 130a-130e of the plurality of sets 130a-130e.

Figure 4:
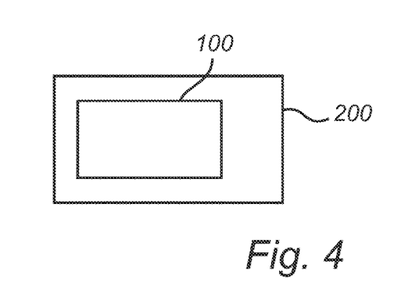
FIG. 4 is a schematic block diagram of a photo-therapy device according to an exemplifying embodiment of the present invention.

Referring now to FIG. 4, there is shown a schematic block diagram of a photo-therapy device 200 according to an exemplifying embodiment of the present invention. The photo-therapy device 200 comprises a light-emitting device 100 such as described with reference to any one of FIGS.

1-3, or in alternative a light-emitting device 105 described in the following with reference to any one of FIGS. 6-8.

Figure 5:
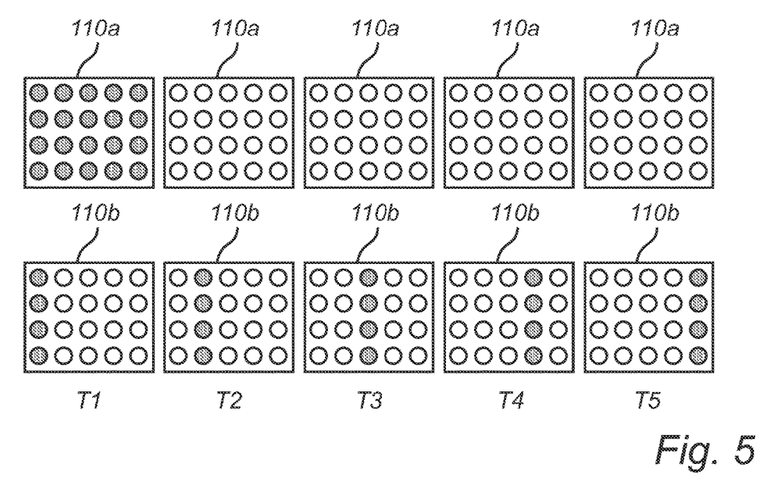
FIG. 5 is a schematic view of light-emitting modules for illustrating principles of the present invention.

Referring now to FIG. 5, there is shown a schematic view of light-emitting modules 110a, 110b for illustrating principles of the present invention.

The upper and lower rows of light-emitting modules 110a, 110b in FIG. 5 indicate the light-emitting module 110a and the light-emitting module 110b, respectively, at different moments in time T1 to T5.

The light-emitting module 110a comprises a single set of light-emitting elements indicated by the plurality of circles within the light-emitting module 110a. The light-emitting module 110b comprises five sets of light emitting elements corresponding to the five columns of light-emitting elements indicated by circles within the light-emitting module 110b.

Each of the light-emitting elements may for example comprise a LED.

In FIG. 5, a filled circle means that the corresponding light-emitting element is activated, i.e. emitting light. An unfilled circle means that the corresponding light-emitting element is deactivated, i.e. not emitting light.

Hence, FIG. 5 illustrates control of the activation and deactivation of light-emitting elements of the light-emitting modules 110a, 100b as a function of time and space.

Considering first the light-emitting module 110a in the upper row of light-emitting modules 110a in FIG. 5, at time T1 all of the light-emitting elements of the light-emitting module 110a are activated and emit light. At times T2 to T5 all of the light-emitting elements of the light-emitting module 110a are deactivated and hence do not emit light. The duty cycle of the light-emitting module 110a is ⅕.

Consider now the light-emitting module 110b in the lower row of light-emitting modules 110b in FIG. 5, which light-emitting module 110b is configured in accordance with a light-emitting device (not shown in FIG. 5) according to an embodiment of the present invention. Each set of light-emitting elements of the light-emitting module 110b, corresponding to a respective one of the five different columns of light-emitting elements indicated by circles within the light-emitting module 110b, is activated at different times T1 to T5, i.e. in separate time slots. Clearly, the duty cycle of the light-emitting module 110b is ⅕, the same as for the light-emitting module 110a.

Hence, the duty cycles of the light-emitting module 110a and the light-emitting module 110b are the same, but the maximum power requirement of the light-emitting module 110b is only a fifth of the maximum power requirement of the light-emitting module 110a, since the light-emitting module 110a is required to be able to power all of the light-emitting elements in the light-emitting module 110a simultaneously (at time T1), but the light-emitting module 110b is only required to be able to power one set at a time.

Hence, a light-emitting device (not shown in FIG. 5) having a light-emitting module operating according to the principles of light-emitting module 110a has a higher power capacity requirement compared to a light-emitting module (not shown in FIG. 5) operating according to the principles of light-emitting module 110b with regards to maximum amount of power that can be supplied to the light-emitting module at a given moment in time. Thus, a light-emitting device (not shown in FIG. 5) having a light-emitting module operating according to the principles of light-emitting module 110a may be associated with higher costs of electronics required for manufacturing the light-emitting device compared to a light-emitting module operating according to the principles of light-emitting module 110b, since a light-emitting device having a light-emitting module operating according to the principles of light-emitting module 110a must be able to power or drive all of the light-emitting elements simultaneously. This is in contrast to a light-emitting device having a light-emitting module operating according to the principles of light-emitting module 110b, which must be able to power or drive only one set at a time.

As described above, the five sets of light-emitting elements comprised in light-emitting module 110b, indicated by the five different columns of light-emitting elements indicated by circles within the light-emitting module 110b, can be activated in a sequence with the first set or column activated at time T1, the second set activated at time T2, the third set activated at time T3, the fourth set activated at time T4, and the fifth set activated at time T5.

Particularly in case a light-emitting device comprising light-emitting module 110b is utilized in photo-therapeutic applications, where the light emitted from the light-emitting device is applied to a certain area of the skin of the subject, it may be desired to have an activation and deactivation sequence of the sets of light-emitting module 110b, i.e. an order of pulsed light emission, different from that described with reference to FIG. 5.

For example, in order to reduce local heat power supplied to the skin during treatment, the sets could be activated in a sequence with the first set or column activated at time T1, the third set activated at time T2, the fifth set activated at time T3, the second set activated at time T4, and the fourth set activated at time T5. In this way, the spatial separation between subsequently powered sets of the light-emitting module 110b can be increased or even maximized so as to mitigate or even eliminate overheating of the skin while still delivering a predefined amount of irradiance to the treated area.

Further reference is made to FIG. 5. On one hand, at time T1 all of the light-emitting elements of the light-emitting module 110a are activated and emit light, which may cause overheating of the treated area. On the other hand, the different sets of the light-emitting module 110b are activated sequentially, thereby delivering the same total amount of radiation as light-emitting module 110a over the period from T1 to T5 to the treated area, but distributed over time and in space.

It is to be understood that the activation and deactivation sequence of the sets of light-emitting module 110b may comprise an activation and deactivation sequence different than those described above as examples, so as to achieve minimal adjacencies of subsequently powered sets of the light-emitting module 110b in time and space. For example, in still another embodiment of the invention, maximal adjacencies of subsequently powered sets of the light-emitting module may be targeted. A light-emitting module may comprise multiple sets of interweaved patterns of light-emitting elements, in a particular example it may be sets of light-emitting elements configured in a checkerboard pattern. The advantage of interweaved sets of light-emitting elements is that substantially the full irradiation area of the light-emitting module may be irradiated with each individual set of light-emitting elements. Irrespective of the specific set of light-emitting elements powered or active at a given time, the delivered spatial light distribution across substantially the full irradiation area of the light-emitting module is relative uniform with only incremental spatial shift when switching power between interweaved sets of light-emitting elements. In other words, the power switching is realized in such an order so as to minimize average spatial separation between subsequently powered sets of the plurality of sets on basis of the arrangement of the plurality of sets relatively to each other in the light-emitting device. In an interweaved embodiment the power requirement reduction is realized in a similar way as discussed previously with reference to FIG. 5, i.e. in proportion to the number of sets of light-emitting elements individually powered and possibly controlled via a control module, but the thermal load to the skin, when the light-emitting module is used in a light-emitting device for skin treatment, is managed differently. When using interweaved sets, the thermal load is nearly continuously present across substantially the full irradiation area but at a lower average level.

Figure 6:
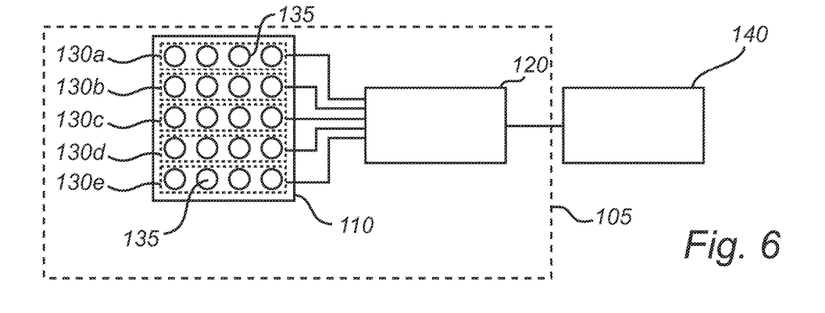
FIGS. 6-8 are schematic block diagrams of light-emitting devices according to embodiments of the present invention.

Referring now to FIG. 6, there is shown a schematic block diagram of a light-emitting device 105 according to an exemplifying embodiment of the present invention.

The light-emitting device 105 comprises a light-emitting module 110 and a power module 120. The light-emitting module 110 comprises a plurality of sets 130a-130e of light-emitting elements 135, indicated by circles in FIG. 6. Only a few of the light-emitting elements 135 shown in FIG. 6 are indicated by reference numerals. A light-emitting element 135 may for example comprise a LED.

Five sets 130a-130e of light-emitting elements 135 are shown in FIG. 6, where each set 130a-130e comprises four light-emitting elements 135. However, it is to be understood that the number of sets included in the light-emitting module 110 and the number of light-emitting elements 135 included in each set 130a-130e, respectively, in principle can be any positive integer, such as two, three, four, six, eight, ten, fifteen, twenty, thirty or fifty or larger.

The power module 120 is adapted to selectively convey, i.e. supply or provide, electrical power to the plurality of sets 130a-130e during respective non-overlapping time intervals for powering the respective sets 130a-130e.

According to the depicted embodiment, electrical power is generated by a power supply unit 140 connectable to the light-emitting device 105 via the power module 120. The power supply unit 140 may be adapted to supply DC and/or AC. The power module 120 may be configured depending on type(s) of current generated by the power supply unit 140, in order to be able to selectively convey DC and/or AC power to the plurality of sets 130a-130e depending on a possible requirement of the respective light-emitting elements 135.

According to the embodiment depicted in FIG. 6, the plurality of sets 130a-130e of light-emitting elements 135 are arranged so as to emit light over a light emission area (not shown in FIG. 6). The plurality of sets 130a-130e of light-emitting elements 135 are arranged relatively to each other such that different sets 130a-130e of light-emitting elements 135 emit light over different portions of the light emission area.

Optionally, similarly to either of the embodiments described with reference to FIGS. 1-3, the power module 120 of the light-emitting device 105 in FIG. 6 may be configured such that it has an upper capacity limit with respect to electrical power that can be conveyed to each of the plurality of sets 130a-130e. The upper capacity limit of the power module 120 may correspond to electrical power requirement of a set 130a-130e of the plurality of sets 130a-130e having a maximum number of light-emitting elements 135 included therein with respect to the number of light-emitting elements 135 included in the respective sets 130a-130e. The power module 120 may comprise an electrical current driver 120 adapted to selectively convey electrical current to the plurality of sets 130a-130e during respective non-overlapping time intervals. The electrical current driver 120 may be configured such that it has an upper capacity limit of electrical current that can be conveyed to the plurality of sets 130a-130e corresponding to electrical current requirement of a set of the plurality of sets having a maximum number of light-emitting elements included therein with respect to the number of light-emitting elements included in the respective sets.

The power module 120 may include its own power supply and hence a separate power supply unit 140 to which the power module 120 is connectable as shown in FIG. 6 may not be required. The power supply 140 may comprise an internal power source, e.g. a battery (not shown in FIG. 6), or be electrically coupled to an external power source, e.g. a power grid (not shown in FIG. 6).

Figure 7:
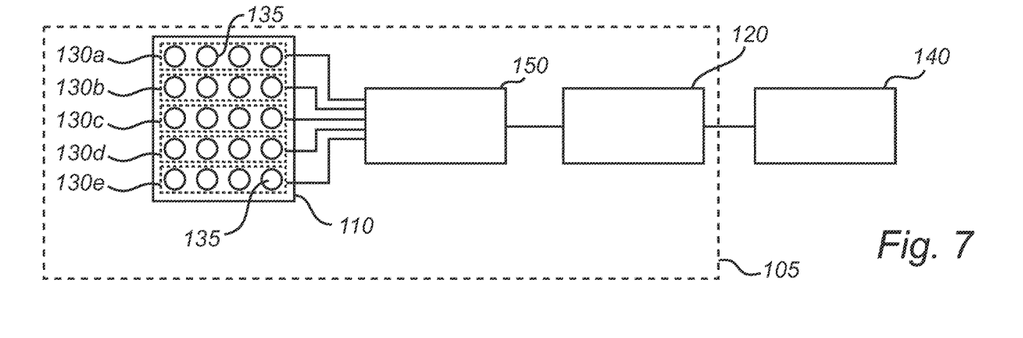

Referring now to FIG. 7, there is shown a schematic block diagram of a light-emitting device 105 according to another exemplifying embodiment of the present invention.

Components indicated in FIG. 7 having corresponding reference numerals to components indicated in FIG. 6 are similar to or the same as the respective components described with reference to FIG. 6, and the functions thereof are similar to or the same as the functions of the respective components described with reference to FIG. 6.

For facilitating effectuating conveyance or supply of power to the respective sets 130a-130e of the plurality of sets 130a-130e, the light-emitting device 105 comprises a current and/or power multiplexer 150. The current and/or power multiplexer 150 is adapted to selectively channel or convey electrical current and/or power to the at least momentarily selected set 130a-130e of the plurality of sets 130a-130e, i.e. the set 130a-130e that is to be at least momentarily powered.

Figure 8:
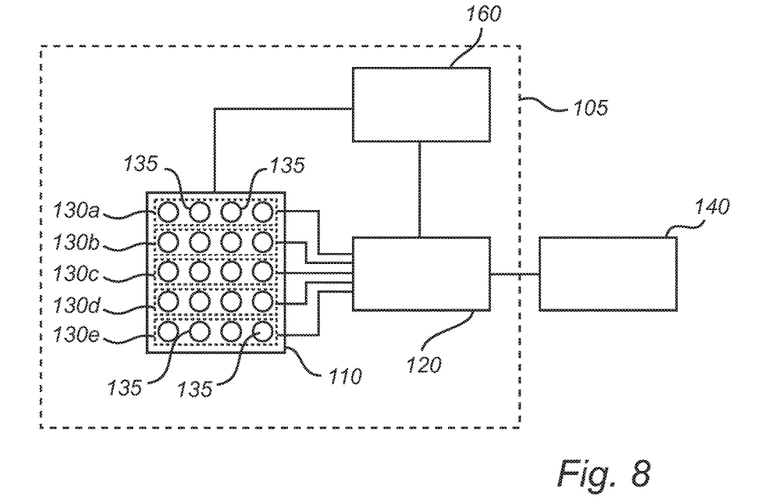

Referring now to FIG. 8, there is shown a schematic block diagram of a light-emitting device 105 according to another exemplifying embodiment of the present invention.

Components indicated in FIG. 8 having corresponding reference numerals to components indicated in FIG. 6 are similar to or the same as the respective components described with reference to FIG. 6, and the functions thereof are similar to or the same as the functions of the respective components described with reference to FIG. 6.

The light-emitting device 105 comprises a control module 160. The control module 160 is adapted to control operation of the power module 120 and, optionally, the light-emitting module 110. The control module 160 can control operation of the light-emitting module 110 and the power module 120 independently of each other.

Figure 9:
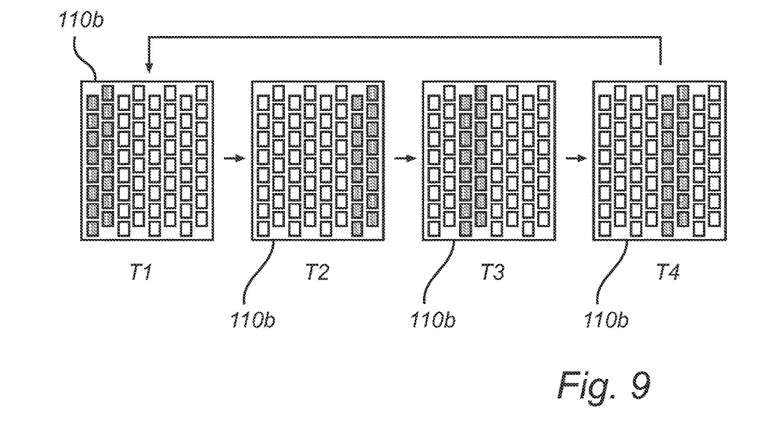
FIGS. 9-11 are schematic views of light-emitting modules for illustrating principles of embodiments of the present invention.

Referring now to FIG. 9, there is shown a schematic view of a light-emitting module 110b for illustrating principles of an embodiment of the present invention.

The row of light-emitting modules 110b in FIG. 9 indicate the light-emitting module 110b, respectively, at different instants or moments in time, or during different time periods, T1 to T4.

As illustrated in FIG. 9, the light-emitting module 110b comprises light-emitting elements indicated by squares within the light-emitting module 110b. According to the exemplifying embodiment depicted in FIG. 9, the light-emitting elements are arranged in eight columns of light-emitting elements in the light-emitting module 110b. The two left-most columns in the light-emitting module 110b constitute a first set of light-emitting elements, the next two columns to the right constitute a second set of light-emitting elements, the next two columns to the right constitute a third set of light-emitting elements, and the two right-most columns in the light-emitting module 110b constitute a fourth set of light-emitting elements. Each of the light-emitting elements may for example comprise a LED. The arrangement of the sets of light-emitting elements and the number of sets of light-emitting elements in the light-emitting module 110b are both according to examples. For example, the number of columns of light-emitting elements is not limited to eight but may in principle be any positive integer, e.g., four, six, seven, nine or ten or larger. The number of light-emitting elements in each column is not limited to that illustrated in FIG. 9 but may in principle be any positive integer. In FIG. 9, a dark square means that the corresponding light-emitting element is activated, i.e. emitting light, and a light square means that the corresponding light-emitting element is deactivated, i.e. not emitting light. Hence, FIG. 9 illustrates control of the activation and deactivation of light-emitting elements of the light-emitting module 110b as a function of time and space.

The sets of light-emitting elements are arranged so as to emit light over a light emission area. The sets of light-emitting elements are arranged relatively to each other such that different sets of light-emitting elements emit light over different portions of the light emission area.

In the first time period T1, the two left-most columns of light-emitting elements, i.e. the first set of light-emitting elements, are emitting light while the remaining sets of light-emitting elements are deactivated. After the time period T1 has expired, the first set of light-emitting elements is deactivated, and another set of light-emitting elements is activated, e.g. the fourth set of light-emitting elements as illustrated in FIG. 9, in the second time period T2. Between T1 and T2 there may be an idle time period when none of the sets of light-emitting elements is activated. After the time period T2 has expired, the fourth set of light-emitting elements is deactivated, and another set of light-emitting elements is activated, e.g. the second set of light-emitting elements as illustrated in FIG. 9, in the third time period T3. Between T2 and T3 there may be an idle time period when none of the sets of light-emitting elements is activated. After the time period T3 has expired, the second set of light-emitting elements is deactivated, and another set of light-emitting elements is activated, e.g. the third set of light-emitting elements as illustrated in FIG. 9, in the time period T4. Between T3 and T4 there may be an idle time period when none of the sets of light-emitting elements is activated.

Thus, the sets of light-emitting elements are activated sequentially, possibly with pauses between activations of different sets of light-emitting elements, and/or possibly until all sets of light-emitting elements have been activated during a respective time period at least once. If required or desired, the cycle of activation of the sets of light-emitting elements during respective time periods may start again.

The duration of each of T1 to T4 may for example be about one to five minutes.

The possible idle time period between T1 and T2, between T2 and T3, and/or between T3 and T4, may for example be about five to twenty times the duration of either of T1 to T4, e.g. about five to hundred minutes.

According to the embodiment depicted in FIG. 9, the portion of the light-emission area that is emitting light at a given time is 25% of the total light-emission area. However, in general, the plurality of sets of light-emitting elements may be arranged relatively to each other such that each of the portions of the light emission area constitutes a fraction of the total light emission area that is less than or equal to 25% of the total light emission area, preferably such that each of the portions of the light emission area constitutes a fraction of the total light emission area that is between 5% and 20% of the total light emission area.

Figure 10:
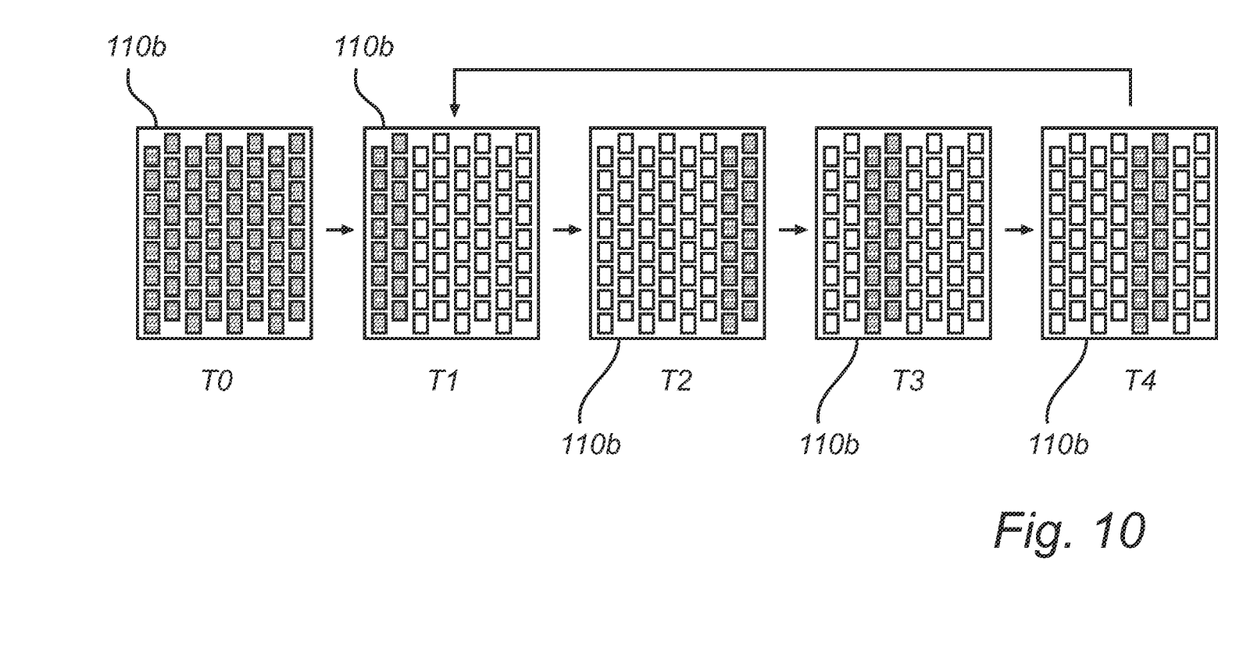

Referring now to FIG. 10, there is shown a schematic view of a light-emitting module 110b for illustrating principles of an embodiment of the present invention.

The embodiment illustrated in FIG. 10 differs from the embodiment illustrated in FIG. 9 in that the cycle of activation of the sets of light-emitting elements during respective time periods T1 to T4 is performed after a time period or instant T0 during which all of the sets of light-emitting elements are powered simultaneously. Thereby, there may be facilitated an increase in vasodilation in a subject illuminated by the light-emitting device to an elevated level, exceeding a normal, nominal or baseline vasodilation level, or maintaining an elevated vasodilation level, prior to the cycle of activation of the sets of light-emitting elements during respective time periods T1 to T4 has begun.

Figure 11:
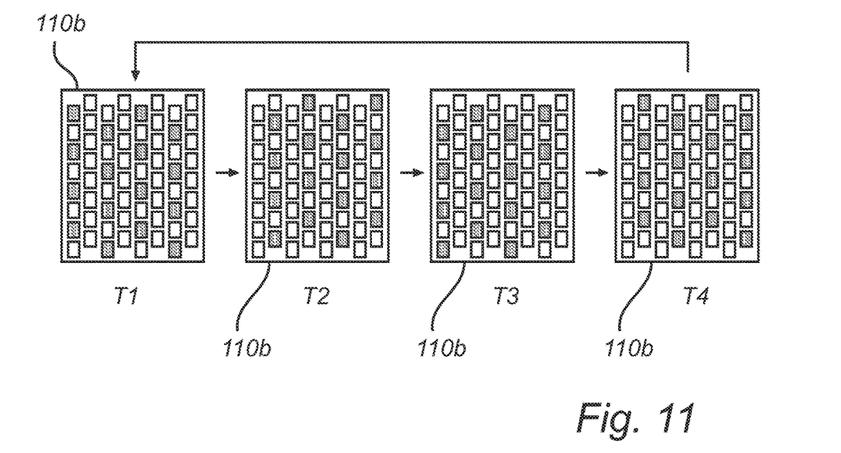

Referring now to FIG. 11, there is shown a schematic view of a light-emitting module 110b for illustrating principles of an embodiment of the present invention.

The embodiment illustrated in FIG. 11 differs from the embodiment illustrated in FIG. 9 in the arrangement of the plurality of sets of light-emitting elements relatively to each other. According to the embodiment depicted in FIG. 11, the sets of light-emitting elements that are activated during respective time periods T1 to T4 are arranged such that each of the portions of the light emission area comprises subportions that are spatially separated with respect to each other. As in FIG. 9, in FIG. 11 a dark square means that the corresponding light-emitting element is activated, i.e. emitting light, and a light square means that the corresponding light-emitting element is deactivated, i.e. not emitting light. Thus, according to the embodiment depicted in FIG. 11, the sets of light-emitting elements form respective "dot patterns" which are non-coinciding with respect to each other and which are activated one at a time during the respective time periods T1 to T4. However, other arrangements of the plurality of sets of light-emitting elements relatively to each than the arrangements illustrated in FIGS. 9 and 10 are possible.

Figure 12:
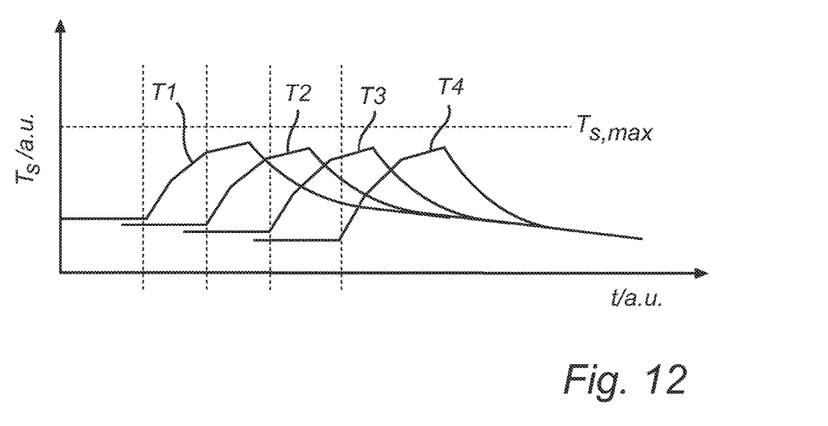
FIG. 12 is graphs of skin temperature $T_s$ versus time t in skin portions of a subject in accordance with an embodiment of the present invention.

In FIG. 12, there is shown graphs of skin temperature $T_s$ versus time t in skin portions of a subject, which skin portions are illuminated by the portions of the light-emission area corresponding to the different sets of light-emitting elements in the light-emitting module 110b in FIG. 9, respectively. Both $T_s$ and t are given in arbitrary units (a.u.). The different graphs in FIG. 12 correspond to the skin portions illuminated during the time periods T1 to T4, respectively, and are labeled accordingly. The position along the horizontal axis where the maximum of each of the graphs occurs represents the time when the respective period T1 to T4 expires, i.e. when the corresponding skin portion ceases to be illuminated. $T_{s,\ max}$ is a threshold temperature value above which the skin temperature is not allowed to exceed. As illustrated in FIG. 12, after illumination of the respective skin portion has ceased, it may take some time for the body to spread the heat caused by the illumination of the respective skin portion, and hence to lower the skin temperature of the respective skin portion to a normal, nominal or baseline skin temperature. During such thermal relaxation, vasodilation may still be at an elevated level, i.e. exceeding a normal, nominal or baseline level.

Figure 13:
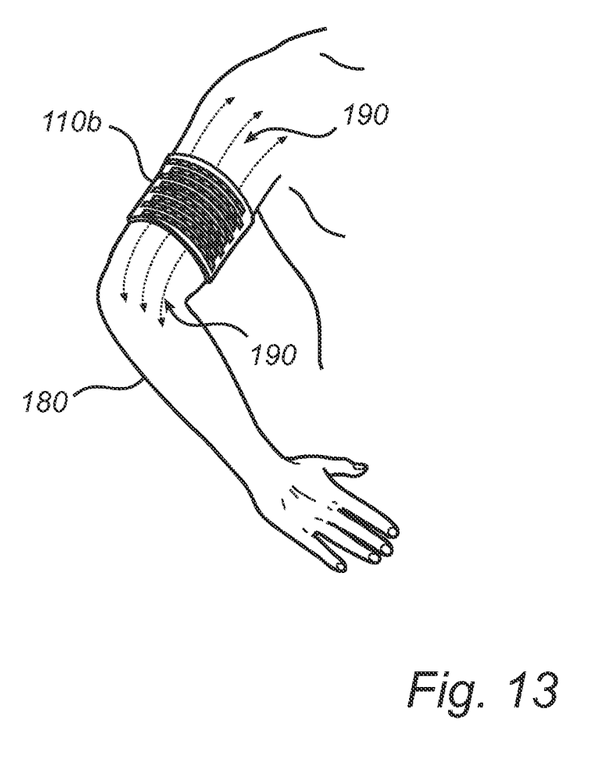
FIG. 13 is a schematic view of a light-emitting module in accordance with an embodiment of the present invention.

Referring now to FIG. 13, there is shown a view of a light-emitting module 110b in accordance with an embodiment of the present invention. The light-emitting module 110b is included in a light-emitting device (not shown in FIG. 13) suitable for use in photo-therapeutic or cosmetic applications. The plurality of sets of light-emitting elements of the light-emitting module 110b are arranged such that the light-emitting device is adapted to generate heat in a skin portion of the arm 180 of a subject caused by the light-emitting device emitting light over the light emission area onto the skin portion. The light-emitting elements of each set of the plurality of sets of light-emitting elements are arranged so as to extend along a direction perpendicular to a main blood flow direction in the arm 180 when the light-emitting device emits light over the light emission area onto the skin. The main blood flow directions in the arm 180 are schematically indicated at 190.

In conclusion, a light-emitting device is disclosed. The light-emitting device comprises a plurality of light-emitting elements or light sources and a power module adapted to selectively convey, supply or provide electrical power to the light-emitting elements. The power module may be dimensioned such as to be able to power only a proper subset of the light-emitting elements of the light-emitting device at a given time, the subset having a maximum number of light-emitting elements included therein with respect to the number of light-emitting elements included in other subsets of the light-emitting elements of the light-emitting device. The plurality of sets of light-emitting elements may be arranged so as to emit light over a light emission area, and the plurality of sets of light-emitting elements may be arranged relatively to each other such that different sets of light-emitting elements emit light over different portions of the light emission area.

While the present invention has been illustrated and described in detail in the appended drawings and the foregoing description, such illustration and description are to be considered illustrative or exemplifying and not restrictive; the present invention is not limited to the disclosed embodiments. Other variations to the disclosed embodiments can be understood and effected by those skilled in the art in practicing the claimed invention, from a study of the drawings, the disclosure, and the appended claims. The mere fact that certain measures are recited in mutually different dependent claims does not indicate that a combination of these measured cannot be used to advantage. Any reference signs in the claims should not be construed as limiting the scope.

The invention claimed is:

1. A light-emitting device comprising:
    a light-emitting module comprising a plurality of sets of light-emitting elements, wherein at least two of said sets have a different number of light-emitting elements;
    a power module adapted to selectively convey electrical power to the plurality of sets during respective non-overlapping time intervals for powering the respective sets;
    a control module being adapted to control the power module to convey power to the plurality of sets during respective non-overlapping time intervals until power has been conveyed to each set of the plurality of sets at least once;
    wherein the power module is configured such that it has an upper capacity limit with respect to an electrical power that can be conveyed to the plurality of sets, the upper capacity limit corresponding to an electrical power requirement of a largest set, having a maximum number of light-emitting elements, of the plurality of sets at a given momenta and
    wherein the plurality of sets of light-emitting elements are arranged to provide spatially interweaved sets of light-emitting elements and the control module is adapted to convey power to the plurality of sets in such an order so as to minimize average spatial separation between subsequently powered sets of the plurality of sets on basis of the interweaved arrangement of the plurality of sets relatively to each other in the light-emitting device.

2. A light-emitting device according to claim 1, wherein the plurality of sets of light-emitting elements are arranged so as to emit light over a light emission area, and the plurality of sets of light-emitting elements are arranged relatively to each other such that different sets of light-emitting elements emit light over different portions of the light emission area.

3. A light-emitting device according to claim 1, wherein the control module is adapted to cause the power module to convey power consecutively to the plurality of sets.

4. A light-emitting device according to claim 3, wherein the control module is further adapted to convey power to the plurality of sets in such an order so as to maximize average spatial separation between subsequently powered sets of the plurality of sets on basis of the arrangement of the plurality of sets relatively to each other in the light-emitting device.

5. A light-emitting device according to claim 1, wherein the control module is adapted to cause the power module to convey power to the plurality of sets during respective non-overlapping time intervals such that there is a temporal distance between conveyances of power to subsequently powered sets of the plurality of sets.

6. A light-emitting device according to claim 1, wherein the control module is adapted to convey power to the plurality of sets in such an order so as to maximize average spatial separation between subsequently powered sets of the plurality of sets on basis of the arrangement of the plurality of sets relatively to each other in the light-emitting device.

7. A light-emitting device according to claim 1, wherein the power module is further adapted to continuously convey additional electrical power to the plurality of sets.

8. A photo-therapy device including a light-emitting device according to claim 1.

9. A photo-therapy device according to claim 8, wherein the light-emitting device is adapted to emit light onto a skin portion of a subject and the photo-therapy device is arranged so as to be releasably connectable to the skin portion.

* * * * *